(12) United States Patent
Boehringer et al.

(10) Patent No.: US 8,022,266 B2
(45) Date of Patent: Sep. 20, 2011

(54) METHOD OF TREATING A WOUND UTILIZING SUCTION

(75) Inventors: John R. Boehringer, Wynnewood, PA (US); John Karpowicz, Chester Springs, PA (US); Amitabha Mitra, Voorhees, NJ (US); Christopher L. Radl, Malvern, PA (US)

(73) Assignee: Boehringer Technologies, L.P., Norristown, PA (US)

( * ) Notice: Subject to any disclaimer, the term of this patent is extended or adjusted under 35 U.S.C. 154(b) by 0 days.

(21) Appl. No.: 12/469,332

(22) Filed: May 20, 2009

(65) Prior Publication Data

US 2009/0287129 A1 Nov. 19, 2009

Related U.S. Application Data

(62) Division of application No. 10/982,346, filed on Nov. 5, 2004, now Pat. No. 7,884,258.

(60) Provisional application No. 60/561,745, filed on Apr. 13, 2004.

(51) Int. Cl.
*A61F 13/00* (2006.01)
*A61F 15/00* (2006.01)
*A61F 13/02* (2006.01)
*A61K 9/70* (2006.01)
*A61L 15/00* (2006.01)
*A61L 15/16* (2006.01)
*A61M 13/00* (2006.01)
*A61M 1/00* (2006.01)
*A61M 27/00* (2006.01)

(52) U.S. Cl. .......... 602/47; 602/42; 602/43; 602/44; 602/45; 602/48; 602/59; 602/76; 424/443; 424/445; 424/446; 424/447; 424/448; 424/449; 604/304; 604/305; 604/306; 604/307; 604/308; 604/313; 604/315; 604/317; 604/540; 604/543

(58) Field of Classification Search .............. 602/42–48, 602/59, 76; 424/443, 445–449; 604/304–308, 604/313, 315, 317, 540, 543
See application file for complete search history.

(56) References Cited

U.S. PATENT DOCUMENTS 2,122,121 A 6/1938 Tillotson
(Continued)

FOREIGN PATENT DOCUMENTS

EP 0619105 A1 10/1994
(Continued)

OTHER PUBLICATIONS

KO; Fabrics, Encyclopedia of Biomaterials and Biomedical Engineering, 2004, Draft Copy, pp. 1-38.
(Continued)

*Primary Examiner* — Michael Brown
*Assistant Examiner* — Brandon Jackson
(74) *Attorney, Agent, or Firm* — Caesar, Rivise, Bernstein, Cohen & Pokotilow, Ltd.

(57) ABSTRACT

A therapeutic device for promoting the healing of a wound in a mammal is disclosed. An exemplary device comprises a permeable structure having a plurality of depressions formed in a surface thereof. In use, the surface having the depressions is disposed adjacent a surface of the wound. A method of treating a wound comprises the steps of providing a permeable structure comprising a plurality of randomly disposed fibers and having i) a plurality of wound surface contact elements disposed between end portions of the structure, and ii) a plurality of voids defined by the contact elements; and applying the permeable structure to at least one surface of the wound.

26 Claims, 7 Drawing Sheets

U.S. PATENT DOCUMENTS

| | | | |
|---|---|---|---|
| 2,385,207 A | 9/1945 | Hunn |
| 3,042,037 A | 7/1962 | Scales et al. |
| 3,053,252 A | 9/1962 | Wolf |
| 3,568,675 A | 3/1971 | Harvey |
| 3,602,220 A | 8/1971 | Bunyan |
| 3,616,156 A | 10/1971 | Scholl |
| 3,703,897 A | 11/1972 | Mack et al. |
| 3,790,433 A | 2/1974 | Baron |
| 3,874,387 A | 4/1975 | Barbieri |
| 3,929,135 A | 12/1975 | Thompson |
| 4,180,074 A | 12/1979 | Murry et al. |
| 4,224,945 A | 9/1980 | Cohen |
| 4,252,590 A | 2/1981 | Rasen et al. |
| 4,323,069 A | 4/1982 | Ahr et al. |
| 4,382,441 A | 5/1983 | Svedman |
| 4,533,352 A | 8/1985 | Van Beek et al. |
| 4,542,739 A | 9/1985 | Schafer et al. |
| 4,906,240 A | 3/1990 | Reed et al. |
| 4,969,880 A | 11/1990 | Zamierowski |
| 4,997,425 A | 3/1991 | Shioya et al. |
| 5,034,006 A | 7/1991 | Hosoda et al. |
| 5,100,396 A | 3/1992 | Zamierowski |
| 5,147,338 A | 9/1992 | Lang et al. |
| 5,176,663 A | 1/1993 | Svedman et al. |
| 5,261,893 A | 11/1993 | Zamierowski |
| 5,358,494 A | 10/1994 | Svedman |
| 5,409,472 A | 4/1995 | Rawlings et al. |
| 5,437,651 A | 8/1995 | Todd et al. |
| 5,447,505 A | 9/1995 | Valentine et al. |
| 5,527,293 A | 6/1996 | Zamierowski |
| 5,549,584 A | 8/1996 | Gross |
| 5,633,007 A | 5/1997 | Webb |
| 5,636,643 A | 6/1997 | Argenta et al. |
| 5,645,081 A | 7/1997 | Argenta et al. |
| 5,810,756 A | 9/1998 | Montecalvo |
| 5,919,180 A | 7/1999 | Raimondo |
| 6,071,267 A | 6/2000 | Zamierowski |
| 6,126,701 A | 10/2000 | Calogero |
| 6,203,563 B1 | 3/2001 | Fernandez |
| 6,207,875 B1 | 3/2001 | Lindqvist |
| 6,345,623 B1 | 2/2002 | Heaton et al. |
| 6,458,109 B1 | 10/2002 | Henley et al. |
| 6,520,982 B1 | 2/2003 | Boynton et al. |
| 6,626,891 B2 | 9/2003 | Ohmstede |
| 6,663,584 B2 | 12/2003 | Griesbach et al. |
| 6,682,757 B1 | 1/2004 | Wright |
| 6,685,681 B2 | 2/2004 | Lockwood et al. |
| 6,689,931 B2 | 2/2004 | Etheredge, III |
| 6,695,823 B1 | 2/2004 | Lina et al. |
| 6,737,149 B1 | 5/2004 | Wintermantel et al. |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B1 | 7/2004 | Randolph |
| 6,800,074 B2 | 10/2004 | Henley et al. |
| 6,885,135 B2 | 4/2005 | Kanao et al. |
| 6,897,349 B2 | 5/2005 | Gibbins et al. |
| 6,936,037 B2 | 8/2005 | Bubb et al. |
| 6,951,553 B2 | 10/2005 | Bubb et al. |
| 6,979,324 B2 | 12/2005 | Bybordi et al. |
| 7,070,584 B2 | 7/2006 | Johnson et al. |
| 7,108,683 B2 | 9/2006 | Zamierowski |
| 7,117,869 B2 | 10/2006 | Heaton et al. |
| 7,273,054 B2 | 9/2007 | Heaton et al. |
| 7,338,482 B2 | 3/2008 | Lockwood et al. |
| 7,381,211 B2 | 6/2008 | Zamierowski |
| 7,381,859 B2 | 6/2008 | Hunt et al. |
| 7,385,101 B2 | 6/2008 | Chandra |
| 7,494,482 B2 | 2/2009 | Orgill et al. |
| 7,534,927 B2 | 5/2009 | Lockwood et al. |
| 2001/0031943 A1 | 10/2001 | Urie |
| 2001/0043943 A1 | 11/2001 | Coffey |
| 2004/0002676 A1 | 1/2004 | Siegwart et al. |
| 2004/0006319 A1 | 1/2004 | Lina et al. |
| 2004/0064111 A1 | 4/2004 | Lockwood et al. |
| 2004/0064132 A1 | 4/2004 | Boehringer et al. |
| 2004/0093026 A1 | 5/2004 | Weidenhagen et al. |
| 2004/0122434 A1 | 6/2004 | Argenta et al. |
| 2004/0127837 A1* | 7/2004 | Sigurjonsson .................. 602/42 |
| 2005/0064021 A1 | 3/2005 | Rippon et al. |
| 2005/0070858 A1 | 3/2005 | Lockwood et al. |
| 2005/0209574 A1 | 9/2005 | Boehringer et al. |
| 2006/0041247 A1 | 2/2006 | Petrosenko et al. |
| 2006/0064049 A1 | 3/2006 | Marcussen |
| 2006/0128245 A1 | 6/2006 | Muth et al. |

FOREIGN PATENT DOCUMENTS

| | | |
|---|---|---|
| GB | 2329127 A | 3/1999 |
| WO | 8001139 | 6/1980 |
| WO | 9100718 | 1/1991 |
| WO | 0045761 | 8/2000 |
| WO | 0134079 | 5/2001 |
| WO | 0137922 A3 | 5/2001 |
| WO | 02092783 A2 | 11/2002 |
| WO | 03057070 A2 | 7/2003 |
| WO | 03057071 A2 | 7/2003 |
| WO | 2004037334 A1 | 5/2004 |
| WO | 2005046761 A1 | 5/2005 |
| WO | 2005046762 A1 | 5/2005 |

OTHER PUBLICATIONS

MA, Scaffolds for tissue fabrication, Materialstoday, May 2004, pp. 30-40.

Marois et al., Endothlial Cell Behavior on Vascular Prosthetic Grafts: Effect of Polymer Chemistry, Surface Structure, and Surface Treatment, ASAIO Journal 1999, pp. 272-280.

Saxena et al., Vacuum-Assisted Closure: Microdeformations of Wounds and Cell Proliferation, Plastic and Reconstructive Surgery, Oct. 2004, vol. 114, No. 5, pp. 1086-1096.

Schein et al., The 'sandwich technique' in the management of the open abdomen, Br. J. Surgery, May 1986, vol. 73, No. 5, pp. 369-370.

Svedman et al., A Dressing System Providing Fluid Supply and Suction Drainage Used for Continous and Intermittent Irrigation, Annals of Plastic Surgery, Aug. 1986, vol. 17, No. 2, pp. 125-132.

Williams, Benefit and risk in tissue engineering, Materialstoday, May 2004, pp. 24-29.

International Search Report dated Jun. 20, 2006 regarding International Application No. PCT/US05/08129.

E. Karamuk et al., Tissupor: Development of a structured wound dressing based on a textile composite functionalized by embroidery technology, tissupor_kti.url, published Sep. 2001, downloaded Oct. 6, 2004, Switzerland.

Chariker et al., Effective management of incisional and cutaneous fistulae with closed suction wound drainage, Contempory Surgery, vol. 34, Jun. 1989, pp. 59-63.

Argenta et al., "Vacuum-Assisted Closure: A New Method for Wound Control and Treatment: Clinical Experience", Annals of Plastic Surgery, vol. 38 (1997), pp. 563-577.

* cited by examiner

METHOD OF TREATING A WOUND UTILIZING SUCTION

CROSS REFERENCE TO RELATED APPLICATIONS

This divisional application claims the benefit under 35 U.S.C. §121 of application Ser. No. 10/982,346, filed on Nov. 5, 2004, which in turn claims the benefit under 35 U.S.C. §119(e) of Provisional Patent Application No. 60/561,745, filed on Apr. 13, 2004, the contents all of which are incorporated herein by reference.

FIELD OF THE INVENTION

The invention relates to a device and method for treating wounds. More specifically, the present invention relates to a therapeutic wound contact device.

BACKGROUND OF THE INVENTION

Wound healing is a basic reparative process of the human body. It has been known throughout time that dressing wounds with appropriate materials aids the body's natural regenerative process. Historically, such materials have been made from cotton fibers; e.g. gauze. These dressings are beneficial to the healing process because they insulate damaged tissue from external contaminants and because they remove potentially deleterious wound exudates.

Numerous studies suggest that wound healing depends on the interplay of complex mechanisms involving cell proliferation, migration and adhesion coupled with angiogenesis. Application of traditional gauze or other essentially flat materials are essentially sub-optimal with respect to these mechanisms. Wound healing studies In-vitro carried out in cell culture vehicles that permit cellular function. It is therefore desirable in the practice of wound healing to provide the equivalent of cell culture or a bioreactor system to allow the optimal interplay of cell functions of proliferation, migration and adhesion. Additionally, it is essential to incorporate other bodily functions that encourage the supply of fibronectins, plasma proteins, oxygen, platelets, growth factors, immunochemicals and so forth.

As science and medicine have advanced, the technology incorporated into wound healing devices has improved substantially. Highly absorbent wound dressings capable of absorbing many times their weight in liquids are available. Systems that temporarily seal wounds and utilize suction to remove exudates have found widespread utilization. Dressings incorporating anti-microbial agents and biologic healing agents are common. Devices that provide a moist wound environment for improved healing have been found to be useful.

In spite of the technological gains in wound healing devices and dressings, millions of people still suffer from the chronic wounds. Such chronic wounds are debilitating and can last for years, greatly diminishing the individual's quality of life. Often such wounds result in the loss of a limb. Individuals may even die from complications such as infection.

As such, there is dire need for more effective wound healing devices and methods.

SUMMARY OF INVENTION

To provide for improved wound healing, the present invention is a wound contact material, a method for making the wound contact material, and a method of treatment employing the wound contact material.

According to an exemplary embodiment of the present invention, a therapeutic device for promoting the healing of a wound in a mammal is provided. The device comprises a permeable substrate or structure having a plurality of depressions formed in a surface thereof, wherein said surface having said depressions is disposed in surface contact with the wound.

According to a further exemplary embodiment of the present invention, a therapeutic device for promoting the healing of a wound in a mammal is provided. The device comprises a permeable structure having a plurality of wound surface contact elements disposed between end portions of the structure, and a plurality of voids defined by the contact elements.

According to an additional exemplary embodiment of the present invention, a therapeutic device for promoting the healing of a wound in a mammal, the device comprising a permeable structure comprising a plurality of fibers coupled to one another having a plurality of wound surface contact elements disposed between end portions of the structure and a plurality of voids defined by the contact elements is provided.

According to a yet further exemplary embodiment of the present invention, a therapeutic device for promoting the healing of a wound in a mammal, the device comprising a polyester felt having a plurality of wound surface contact elements disposed between end portions of the structure and a plurality of voids defined by the contact elements is provided.

According to an additional exemplary embodiment of the present invention, a method of manufacturing a therapeutic device for promoting the healing of a wound in a mammal comprises the steps of providing a molten substrate material providing a mold defining a plurality of depressions and a plurality of contact elements and applying the molten substrate material to the mold.

According to an even further exemplary embodiment of the present invention, a method of manufacturing a therapeutic device for promoting the healing of a wound in a mammal comprises the steps of providing a permeable structure and forming a plurality of depressions into a surface of the permeable structure.

According to another exemplary embodiment of the present invention, a method of treating a wound comprises the steps of providing a permeable structure comprising i) a plurality of wound surface contact elements disposed between end portions of the structure, and ii) a plurality of voids defined by the contact elements, and applying the permeable structure to at least one surface of the wound and applying a force to the structure to maintain the structure in intimate contact with the wound surface.

These and other aspects and objects will become apparent from the following description.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following Figures.

DETAILED DESCRIPTION OF THE INVENTION

Figure 1:
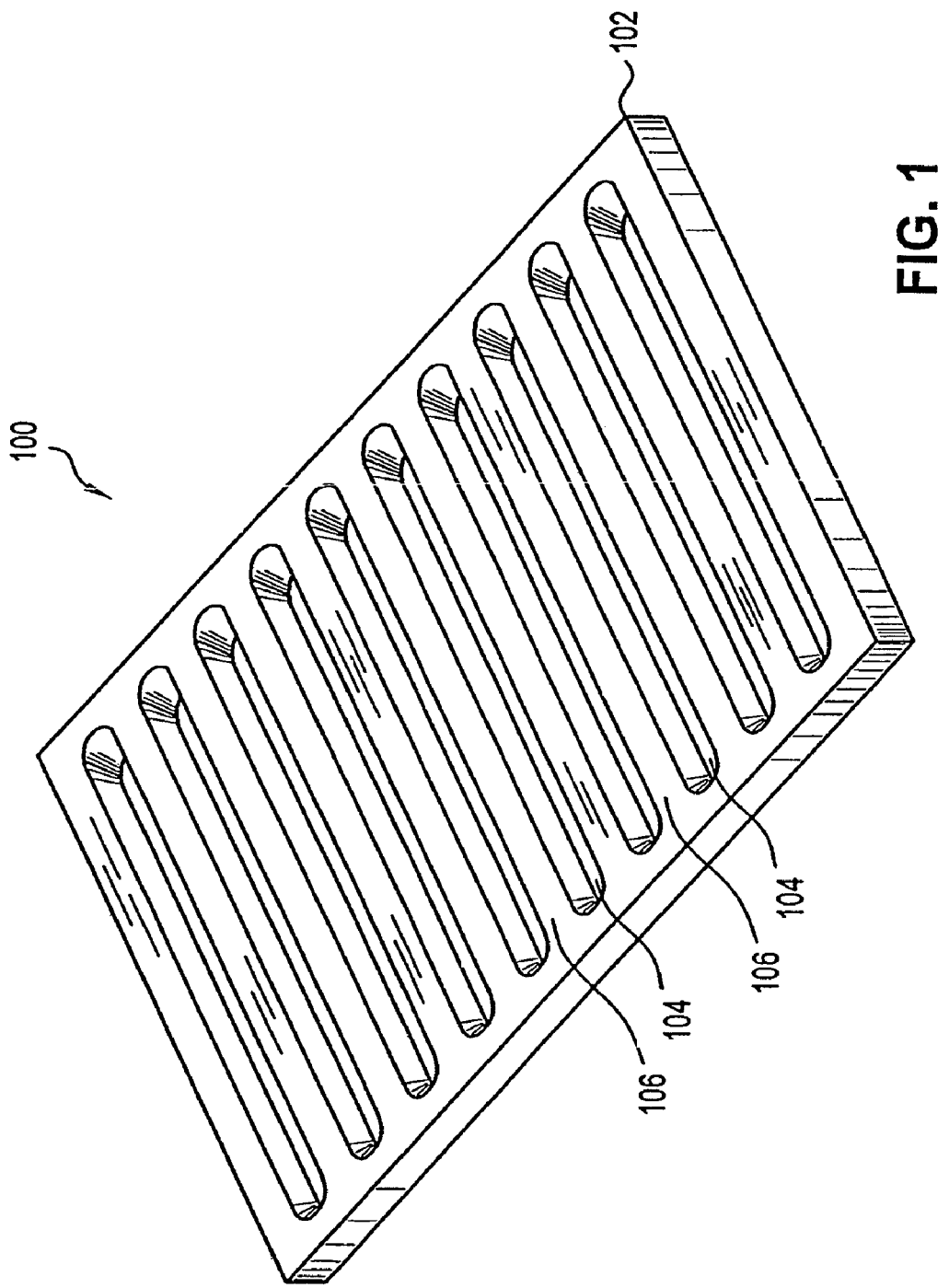
FIG. 1 is a perspective view of a channeled wound contact dressing according to a first exemplary embodiment of the present invention.

A wound dressing with a discontinuous contact layer surface has the advantages of promoting tissue growth with wound surface contact elements and permitting tissue growth by providing void volume for the subsequent tissue growth within the discontinuities. Desirably, the structure of the contact material is sufficiently physically rugged to resist flattening when forces required to press the material against the wound surface are applied to the material.

It is desirable for the material to retain its structure when exposed to aqueous or other bodily fluids. Many traditional dressing materials soften as then moisten so that their geometry changes. The contact layer is permeable, permitting the underlying wound to breathe and allowing for fluids to be drawn from the wound. The contact layer should not be too absorbent as this might result in a loss of structure. The layer is comprised of base materials that are resistant to change in the presence of moisture and aqueous liquids.

In the current embodiment, the extent of the voids remaining above the wound surface is preferably at least 0.1 mm when the structure is pressed against the surface of the wound. The width of the voids, as defined by contact elements adjacent the voids, is preferably greater than 0.1 mm. A more preferred width is between about 0.5 to 10 mm and a more preferred height is between about 0.2 to 5 mm.

Wound healing is recognized as a complex process. When a wound contact material as described is forced against a wound surface, a number of biological processes are believed to occur. Mechanical stress is applied to the underlying tissue. The discontinuities in the contact surface impose a force resulting in a catenary shape on the tissue. These mechanical forces encourage cellular activities as well as angiogenesis, and the discontinuities begin to fill with granular tissue. Excess fluid is conveyed away from the wound and tissue develops in a manner and pattern whereby disruption of the newly developed tissue is minimized upon removal of the contact surface.

A fibrous substrate or structure has all the flexibilities provided by the textile arts. Fibrous textiles can be formed into a structure for the invention by a number of the methods known in the art. Among these methods are knitting, weaving, embroidering, braiding, felting, spunbonding, meltblowing, and meltspinning. Each of these methods can be further adapted to produce a material whose structure matches that of the present invention. The desired structure can be imparted during production of the structure by, for example, applying molten material directly to a mold as in meltblowing. Alternatively, the structure can be formed by working a formed structure after production by, for example, heat stamping or vacuum forming. Further, fibers can be mixed with an adhesive and sprayed onto a textured surface.

The versatility of fibrous textiles also extends to their easy adaptation to composite applications. Individual fiber materials may be varied to optimize a physical parameter such as rigidity or flexibility. Individual fiber materials can also be selected for their known ability to assist in wound healing. Examples of such fiber materials are calcium alginate, and collagen. Alternatively, fibers may be treated with known wound healing agents such as hyaluronic acid and antimicrobial silver. The ratio of the fiber materials can be varied to suit the requirements of the wound. According to one desirable aspect of the invention, different fibers with various wound healing properties may be added as desired.

Other fibrous structures that are anticipated as beneficial additions include:

1. Fluid absorbing fibers
2. Non-adsorbent fibers
3. Bio-absorbable fibers
4. Wicking fibers to wick fluid away from the surface of the wound
5. Fibers with known healing effects, such as calcium alginate
6. Bio-erodable fibers for the controlled release of curative agent
7. Conductive fibers for the delivery of an electric charge or current
8. Adherent fibers for the selective removal of undesirable tissues, substances or microorganisms
9. Non-adherent fibers for the protection of delicate tissue An exemplary embodiment of the present invention is illustrated in FIG. 1. As shown in FIG. 1, channeled wound dressing 100 is comprised of a generally conformable polyester felt material 102. An alternative polyester textile such as knit, weave, or braid may also be suitable for most applications. Polyolefins, such as polyethylene or polypropylene, and polyamides, such as nylon, with similar physical properties are also contemplated. Creep resistance, as exhibited by polyester, is particularly desirable. Void channels 104 are cut into felt material 102 to provide a discontinuity that promotes the upward growth of new tissue. In use, the channeled wound dressing 100 is pressed against a wound in intimate contact with injured tissue. A force of 0.1 psi or more is desirably applied to the contact layer to press the contact elements against the surface of the wound. Wound contact elements 106 are thus in intimate contact with injured tissue.

Figure 2A:
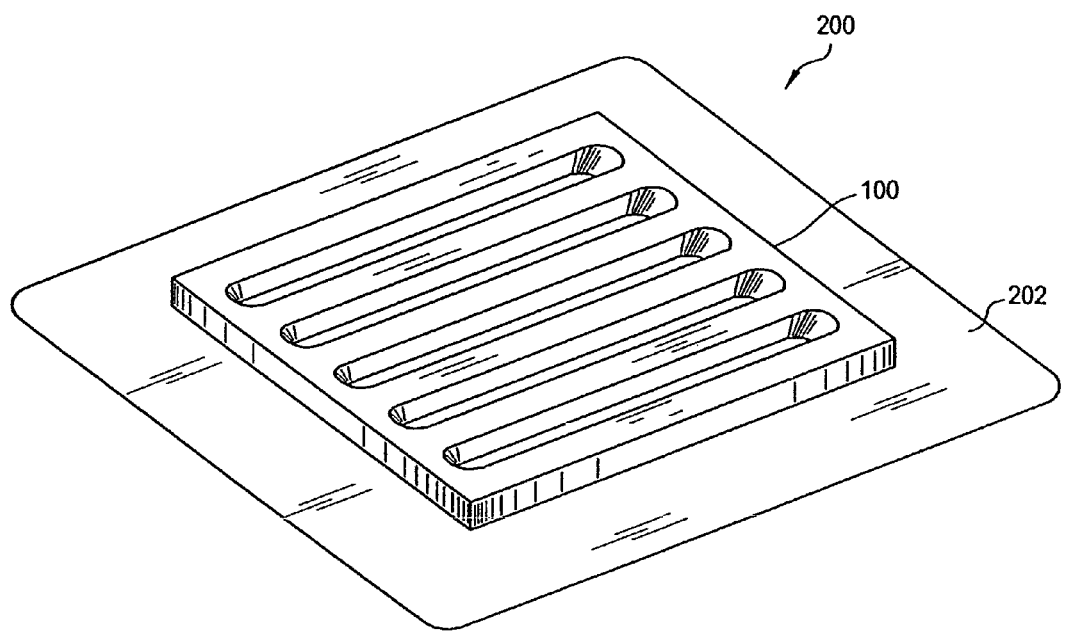
FIG. 2A is a perspective view of a channeled wound contact composite according to a second exemplary embodiment of the present invention.
Figure 2B:
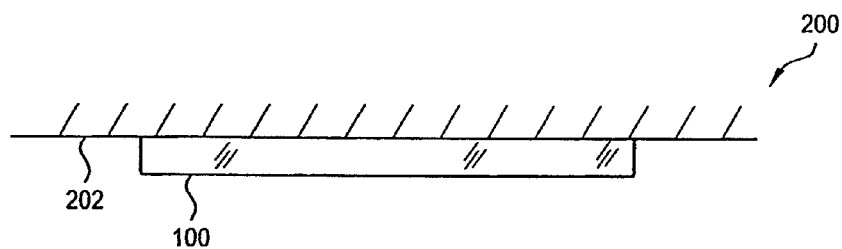
FIG. 2B is a cross section of the channeled wound contact composite according to the second exemplary embodiment of FIG. 2A.

FIGS. 2A and 2B illustrate a wound dressing composite 200 comprised of channeled dressing 100 and a vapor permeable adhesive backed sheet 202. Adhesive backed vapor permeable sheets, in general, are known in the art and are believed to contribute to wound healing by maintaining a moisture level that is optimal for some wounds. In use, dressing composite 200 is placed onto the surface of the wound with its channeled dressing 100 portion in contact with the wound. Adhesive sheet 202 covers channeled dressing 100 and adheres to skin adjacent the wound. Composite 200 offers the advantages of channeled dressing 100. Additionally, adhesive sheet 202 secures composite 200 and protects the wound from bacteria, etc. while allowing for the transmission of moisture vapor.

Figure 3A:
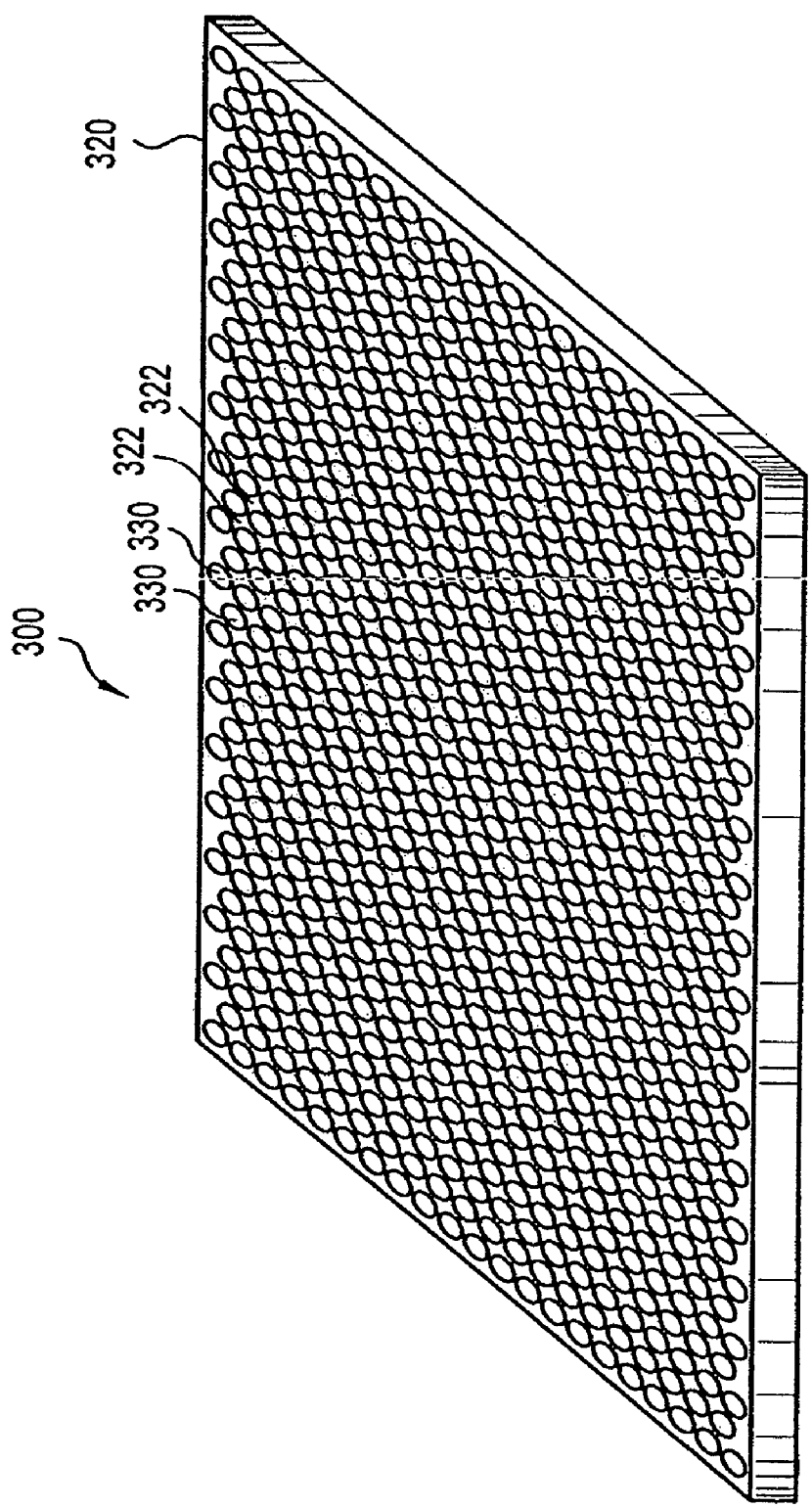
FIG. 3A is a perspective view of a dimpled wound dressing according to a third exemplary embodiment of the present invention.
Figure 3B:
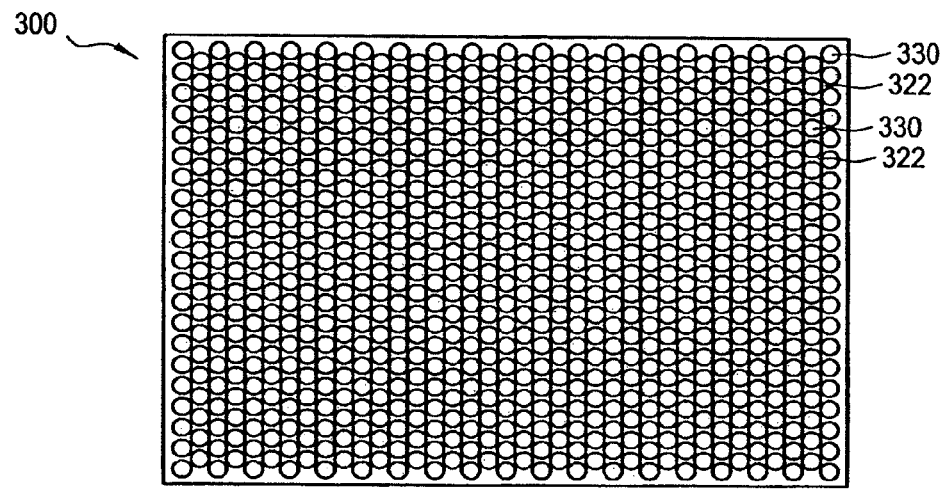
FIG. 3B is a top view of the dimpled wound dressing illustrated in FIG. 3A.
Figure 3C:
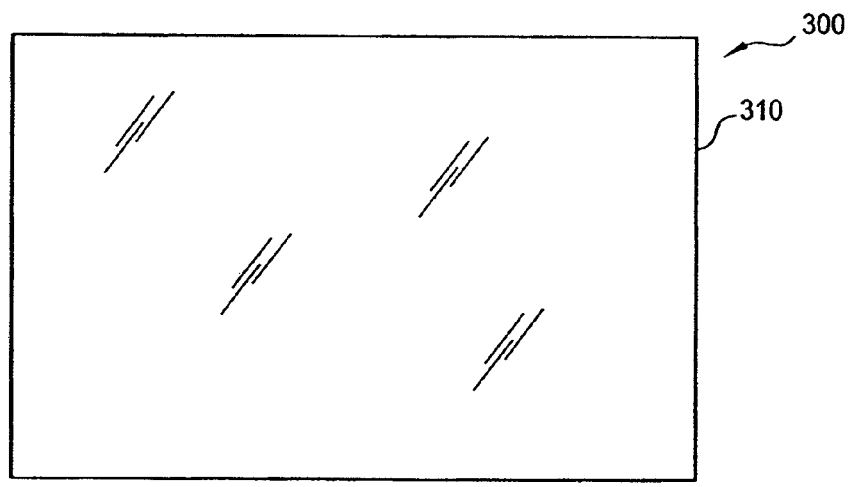
FIG. 3C is a bottom view of the dimpled wound dressing illustrated in FIG. 3A.
Figure 3D:
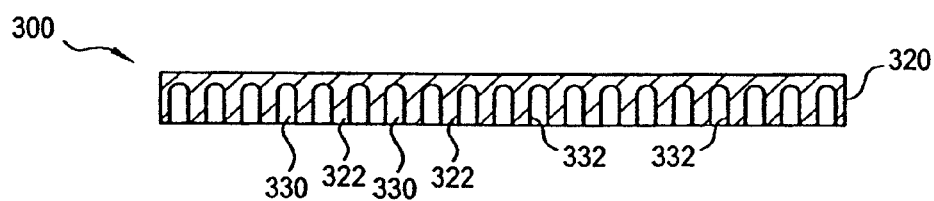
FIG. 3D is a cross sectional view of the dimpled wound dressing illustrated in FIG. 3A.

Another desirable embodiment of the present invention is illustrated in FIGS. 3A, 3B and 3C and 3D. The substrate or structure for dimpled wound dressing 300 can be constructed from similar materials and production methods employed for channeled dressing 100. FIG. 3A depicts a perspective view of dimpled dressing 300 with contact surface 320 on top. FIG. 3D shows a cross section of the dimpled dressing 300 which best illustrates the plurality of contact elements 322 and dimple voids 330. Preferably, the total dimple void area comprises at least about 25% of the total dressing area. More preferably, the total dimple void area comprises at least about 50% of the total dressing area. Dimple voids 330 are partially defined by sidewalls 332. Sidewalls 332 are partially responsible for providing rigidity necessary to resist compaction of dimple dressing 300. Contact elements are preferably constructed to provide an arcuate contact surface. In a preferred embodiment, the radius of contact is between about 0.1 mm to 1 mm.

Dimple voids 330 can be formed in a variety of regular or irregular shapes. Preferably, dimple voids are constructed so that they are not "undercut" such that each aperture circumference is smaller than the corresponding inner void circumference. An "undercut" or reticulated void structure can cause tissue disruption when the dressing 300 is removed because any tissue that has grown into the void may be torn away when the material is removed from the wound. Additionally, undercut or reticulated void structures are more likely to result in shedding of the dressing material into the newly developing wound tissue.

In one preferred embodiment, a base material for dressing 300 is Masterflo RTM manufactured by BBA group of Wakefield, Mass. In this exemplary embodiment, the base material has a thickness of about 1.0 mm. Dimple voids 330 are heat stamped into the base material having a depth of about 0.75 mm and a diameter of about 2 mm.

Because the contact layer is generally replaced every few days it is important to account for the possibility of alignment of newly formed tissue with the voids of a new contact layer. Thus, according to exemplary embodiments of the present invention 1) dimple voids 300 can be arranged randomly so that they don't line up with the new tissue growth after each dressing change, 2) different contact layers with different diameter dimples may be provided, or 3) a different spacing of the dimples can be used every time the material is changed.

FIG. 3B and 3C illustrate the corresponding top and bottom views, respectively, of dimpled dressing 300. One variation of this embodiment is also contemplated having dimple voids 330 and/or contact elements 322 disposed on both the top and bottom of dimpled dressing 300. A second variation on dimpled wound dressing 300 is also contemplated wherein some or all of the dimple voids 330 are replaced with holes traversing the structure's entire thickness such that the top and bottom views of the variation would appear similar to FIG. 3B.

In one exemplary embodiment, dimple voids 330 can be partially filled with therapeutic substances. For example, antiseptic substances might be placed in voids 330 for treating infected wounds. Further, biologic healing agents could be delivered in the voids to improve the rate of new tissue formation. In yet another exemplary embodiment, the layer of dressing 300 could have a different function on each side. For example, one side of dressing 300 could be optimized for the growth of new tissue, while the other side could be optimized for the delivery of anti-microbial agents, for example.

Figure 4A:
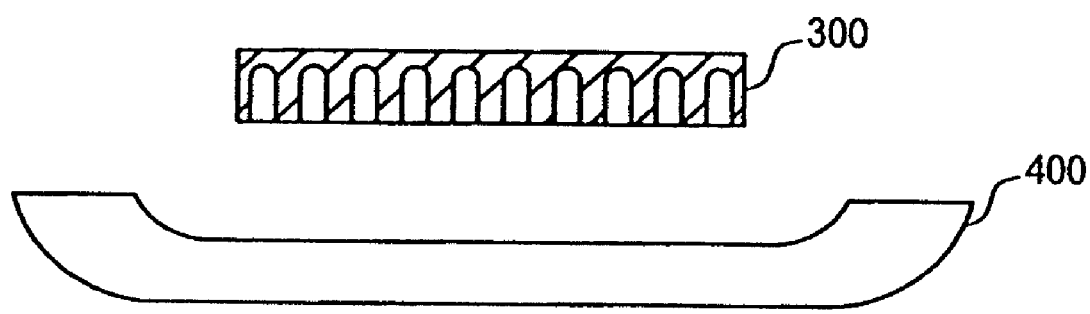
FIGS. 4A, 4B and 4C are illustrations of the dimpled wound dressing of FIG. 3A in use.
Figure 4B:
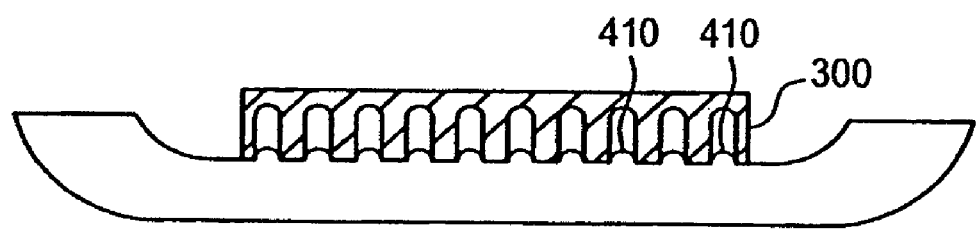
Figure 4C:
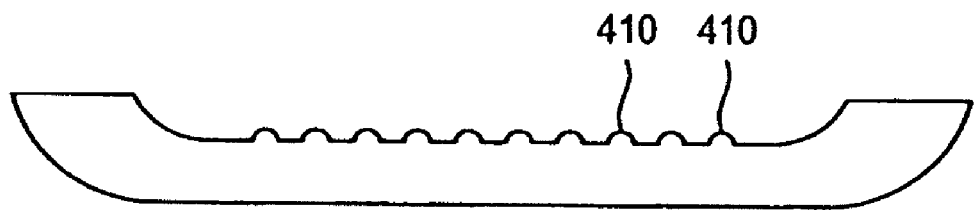

Use of dimpled dressing 300 is illustrated by FIGS. 4A, 4B and 4C. FIG. 4A shows a wound surface 400. Note that wound surface 400 may represent the majority of a shallow surface wound or a small interior portion of a deep tissue wound. FIG. 4B shows application of dimpled dressing 300 to wound surface 400 and corresponding tissue growth 410 within dimple voids 330. Finally, removal of dimpled dressing 300 leaving tissue growth 410 is illustrated in FIG. 4C. As will be addressed in detail below, it is desirable to provide an external force for keeping dressing 300 pressed against the surface of the wound.

Figure 5A:
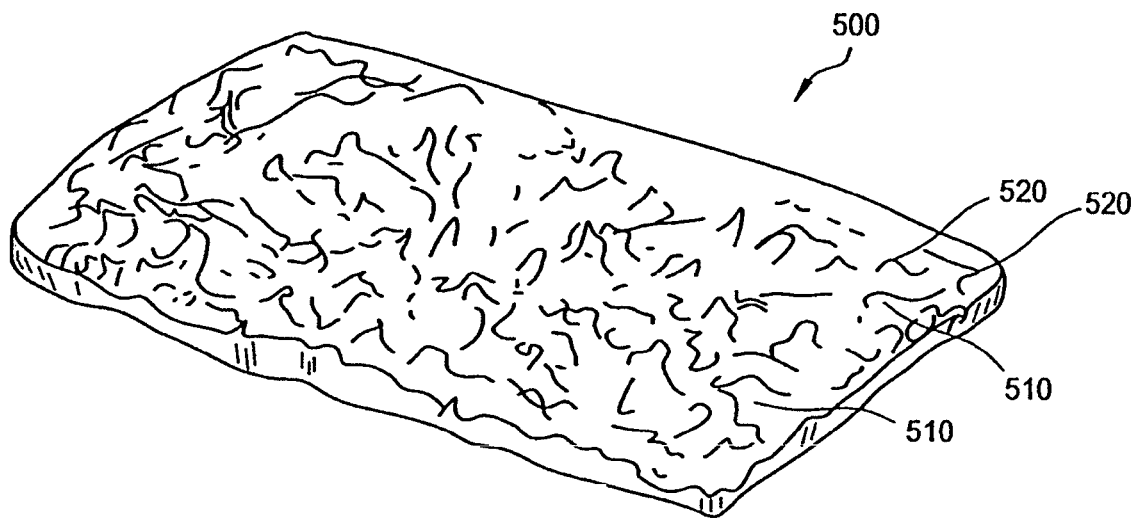
FIG. 5A is a perspective view of an irregular wound contact dressing according to a fourth exemplary embodiment of the present invention.
Figure 5B:
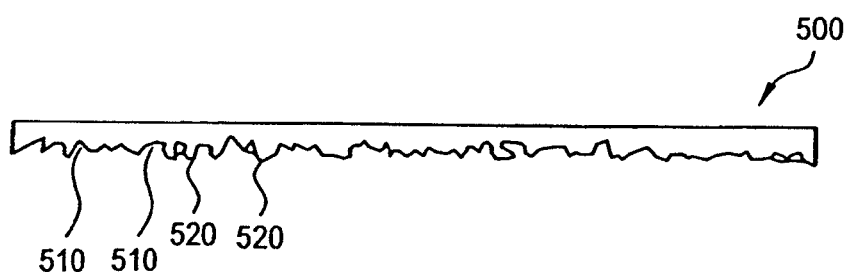
FIG. 5B is a cross sectional view of the irregular wound contact dressing illustrated in FIG. 5A.

FIGS. 5A and 5B illustrate another embodiment of the present invention; a rough irregular dressing 500. From a perspective view, FIG. 5A depicts how irregular dressing 500 has irregular voids 510 and irregular contact elements 520 acting as "hook-like" members that are able to contact and stick to necrotic tissue when the substrate is placed in the wound. When the substrate is removed from the wound, necrotic tissue is stuck to hook like protrusions 520 and is thus removed from the wound. Removal of the substrate debrides the wound. Removal of necrotic tissue is an important part of healing wounds. The substrate of dressing 500 may be made from polyester felt or batting. In one exemplary embodiment, the felt is singed with hot air so that a percentage of the fibers melt to form a textured surface with a number of hook like elements 520. Another suitable configuration can be the hook material such as that used with hook and loop fabric.

After adequate removal of the necrotic tissue, the wound may still be considered infected and can be treated with the substrate including antimicrobial silver, for example, which is useful in killing bacteria, while the substrate and method of use facilitate the growth of new tissue.

The phase of wound healing where new tissue is forming is generally referred to as the proliferative phase. Once the wound is adequately healed in the proliferative phase and the bacterial load is adequately reduced, a substrate without antimicrobial silver and optionally with the addition of growth enhancing materials is used to facilitate the continued proliferation of new cells and tissue.

FIG. 5B shows the random cross section of irregular dressing 500. The roughened surface of irregular dressing 500 can be formed by passing a suitable substrate under convective heat at or about the melting point of the substrate's component material. For example, polyester materials typically melt in a range from about 250 degrees Celsius to about 290 degrees Celsius. A polyester felt material passed briefly under a convective heat source operating in this range will experience surface melting and subsequent fusing of the polyester strands at its surface. The degree of surface melting can be controlled with temperature and exposure time to yield a surface of desired roughness exhibiting irregular voids 510 and irregular contact elements. Although irregular dressing 500 is illustrated as having only one roughened surface the invention is not so limited in that both upper and lower surfaces may be similarly roughened. Such a dressing would be useful in the treatment of an undermined wound.

As described above, treatment with the present wound dressing invention comprises forcing the inventive dressing into intimate contact with the wound surface. Generally the force should be at least 0.1 psi. Various methods and systems for maintaining this intimate contact are contemplated. These methods and systems may include: applying an adhesive film over the inventive dressing and adjacent the wound surface; wrapping a bandage over the dressing and around the injured area; and securing a balloon or another inflatable bladder to the structure and inflating the bladder with air or a liquid. In one exemplary embodiment, the application of pressure to the bladder is provided intermittently. A conformable seal may be placed over the wound and contact structure, a rigid seal is then secured over the wound, contact structure imparting a force on the contact structure. A pressure is then applied between the rigid seal and the flexible seal forcing the contact structure against the wound surface. The intimate contact may be augmented by sealing the wound area with a conformable cover and applying suction. When suction is used, dimpled wound dressing 300 is particularly well-adapted for this application. In general the range of suction levels is between 0.25 psi and 5 psi. The suction use can be further improved by applying a wound packaging material to the back of the dressing. One such suitable wound packaging material is described in U.S. Provisional Patent Application No. 60/554,158, filed on Mar. 18, 2004.

Figure 6:
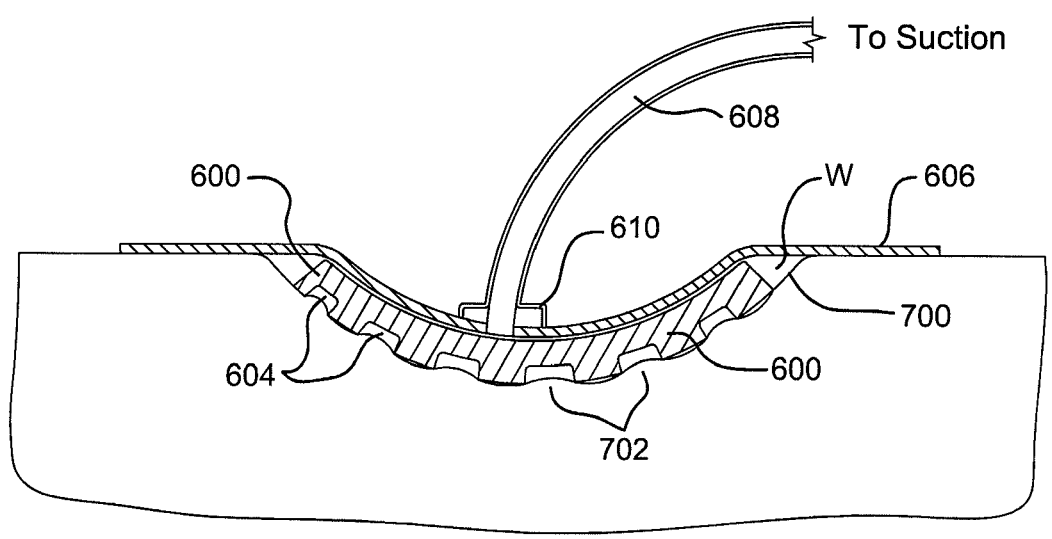
FIG. 6 is a cross sectional view of an exemplary wound contact device in use on a wound.

FIG. 6 illustrates therapeutic device 600 in use in wound W. As shown in FIG. 6, therapeutic device 600 with depressions 604, such as dimple void for example, is placed in wound W with depressions 604 placed adjacent wound surface 700. Wound W and therapeutic device 600 are desirably covered with wound cover 606, such as an adhesive back polyurethane film for example. In one exemplary embodiment, suction from a suction source (not shown) may be applied to wound W via suction tube 608 and coupling 610. As healing progresses, tissue 702 in the wound bed grows into depressions 604.

The depressions 604 remain intact even when the device is placed in a wound and suction is applied. Additionally, where the material of the device is comprised of generally non-absorbent fibers, the material does not get soggy when in a wet wound. This allows the wound fluids to be pulled out of the wound by suction, for example, and additionally ensures that depressions 604 remain. It is critical that the depressions remain, so that voids exist where new tissue can grow filling the wound cavity.

While the above described configuration uses depressions having a dimpled shape, other 3 dimensional structures can be fabricated such that there is a void for tissue to grow in to. One such non-limiting alternative configuration would be a woven waffle pattern.

Case Study 1

Patient A is a 70 year old male with a Stage IV decubitus ulcer on the right hip with significant undermining. The contact structure of the present invention was applied to the wound and an adhesive film was placed over the wound and the contact structure. A suction of 1.1 psi was applied beneath the adhesive film to impart a force upon the contact structure. The suction was maintained generally continuously. The contact material was replaced every two to four days. After use of the device for 30 days the undermined portion of the wound had virtually healed and the area of the wound opening had decreased from 66 square cm to 45 square cm. A split thickness skin graft was applied to the wound.

Case Study 2

Patient B is a 50 year old male with a fracture of the right ankle with exposed bone. A plate was used to reduce the fracture and a rectus abdominus free flap was performed to cover the exposed bone and hardware. The flap only partially survived resulting in an open wound with exposed bone and hardware. The contact structure of the present invention was applied to the wound and an adhesive film was placed over the wound and the contact structure. A force was applied to the contact structure by the application of an ace bandage wrapped around the ankle or by the application of suction. The suction force was generally applied for about half of the day and the force of the bandage wrap was maintained for the remainder of the day. For a number of days, the bandage wrap was solely used to impart the force. When the force was imparted by suction a suction of between 1 and 2 psi was used. In less than 2 weeks new tissue had grown over the exposed hardware. In a period of 7 weeks the wound area was reduced from 50 square cm to 28 square cm.

While preferred embodiments of the invention have been shown and described herein, it will be understood that such embodiments are provided by way of example only. Numerous variations, changes, and substitutions will occur to those skilled in the art without departing from the spirit of the invention. Accordingly, it is intended that the appended claims cover all such variations as fall within the spirit and scope of the invention.

What is claimed is:

1. A method of facilitating the healing of a wound in a mammal by encouraging cellular activity at the wound comprising:
  a. providing a dressing comprising a permeable structure having a first surface, a second surface and a plurality of interstices located between said first surface and said second surface, wherein: (i) said first surface comprises wound surface contact elements and a plurality of discrete voids defined by said wound surface contact elements, (ii) each of said voids is resistant to collapse in the presence of liquids in the wound to maintain empty space therein, and (iii) each of said first surface, said second surface and said wound surface contact elements comprises the same fibrous material;
  b. applying said dressing on the wound so that said first surface is in engagement with the tissue of the mammal at the wound;
  c. providing a cover;
  d. applying said cover over said second surface of said dressing to establish a confined space in which said dressing is located and to cause said first surface of said dressing to be in intimate engagement with the tissue of the mammal at the wound;
  e. providing a vacuum source;
  f. applying suction to said confined space by coupling said vacuum source to said confined space to produce a compressive force on said dressing while maintaining empty space within said voids, whereupon a force in a force range of 0.1 PSI to 5.0 PSI is applied on the tissue at said voids by the suction, which force encourages cellular activity within said voids without completely collapsing said voids, thereby facilitating wound healing; and
  g. maintaining said dressing in intimate engagement with the tissue of the mammal at the wound during the application of suction thereto.

2. The method of claim 1 wherein each of said voids is in communication with at least some of said interstices.

3. The method of claim 2 wherein said voids extend into said permeable structure and wherein each of said voids has a top portion located remotely from said second surface.

4. The method of claim 3 wherein at least some of said interstices are in communication with respective ones of said top portions of said voids.

5. The method of claim 2 wherein said permeable structure consists essentially of said fibrous material.

6. The method of claim 5 wherein said fibrous material is polyester fibers.

7. The method of claim 2 wherein said cover is conformable.

8. The method of claim 7 wherein said cover comprises an adhesive film for forming a conformable seal with the tissue of the mammal adjacent the wound, such that no adhesive is applied to the wound.

9. The method of claim 2 wherein the average depth of said voids is greater than 0.1 mm.

10. The method of claim 9 wherein the average depth of said voids is in the range of 0.2 mm to 5 mm.

11. The method of claim 2 wherein said empty space in said voids when suction is applied to said confined space extends to at least about 0.1 mm above the surface of the wound.

12. The method of claim 11 wherein said empty space in the voids when suction is applied to the confined space extends to within the range of about 0.2 mm to 5 mm above the surface of the wound.

13. The method of claim 2 wherein the suction is applied over at least a several day period of time.

14. The method of claim 13 wherein the suction is applied and maintained substantially continuously during the at least several day period of time.

15. The method of claim 2 wherein said permeable structure comprises a non-woven material.

16. The method of claim 2 wherein said plurality of voids occupies more than about 25% of the surface area of the first surface.

17. The method of claim 2 wherein the average width of said voids is at least 0.1 mm.

18. The method of claim 2 wherein the average width of said voids is within the range of about 0.5 mm and 10 mm.

19. The method of claim 2 wherein said first surface of said dressing is held in intimate engagement with the tissue of the mammal at the wound at least partially by the applied suction.

20. The method of claim 2 additionally comprising providing a wound packing between said second surface of said dressing and said cover.

21. The method of claim 2 wherein the suction is applied and maintained in discrete periods of time of a duration of at least one half of a day.

22. A method of facilitating the healing of a wound in a mammal by encouraging cellular activity at the wound comprising:
   a. providing a dressing comprising a permeable structure having a first surface, a second surface and a plurality of interstices located between said first surface and said second surface, said first surface comprising a plurality of discrete voids, each of said voids being resistant to collapse in the presence of liquids in the wound to maintain empty space therein and being in communication with at least some of said interstices, said plurality of voids occupying more than about 25% of the surface area of said first surface and wherein the average width of said voids is at least 0.1 mm and the average depth of said voids is greater than 0.1 mm;
   b. applying said dressing on the wound so that said first surface is in engagement with the tissue of the mammal at the wound;
   c. providing a conformable cover comprising an adhesive film arranged for forming a conformable seal with the tissue of the mammal adjacent the wound without applying any adhesive to the wound;
   d. applying said cover over said second surface of said dressing to establish a confined space in which said dressing is located and to cause said first surface of said dressing to be in intimate engagement with the tissue of the mammal at the wound;
   e. providing a vacuum source;
   f. applying and maintaining suction of substantially continuously over at least a several day period of time from said vacuum source to said confined space by coupling said vacuum source to said confined space to produce a compressive force on said dressing while maintaining some empty space within said voids extending to at least about 0.1 mm above the surface of the wound, whereupon a force in a force range of 0.1 PSI to 5.0 PSI is applied on the tissue at said voids by the suction, which force encourages cellular activity within said voids without completely collapsing said voids, thereby facilitating wound healing; and
   g. maintaining said dressing in intimate engagement with the tissue of the mammal at the wound during the application of suction thereto.

23. The method of claim 22, wherein the discrete voids are defined by wound surface contact elements of the first surface, and each of said first surface, said second surface and said wound surface contact elements comprises the same fibrous material.

24. The method of claim 23, wherein said permeable structure consists essentially of said fibrous material.

25. A method of facilitating the healing of a wound in a mammal by encouraging cellular activity at the wound comprising:
   a. providing a dressing comprising a permeable structure having a first surface, a second surface and a plurality of interstices located between said first surface and said second surface, said first surface comprising wound surface contact elements and a plurality of discrete voids defined by the wound surface contact elements, each of said voids extending into said permeable structure and having a top portion located remotely from said second surface, with at least some of said interstices being in communication with respective ones of said top portions of said voids, with the average width of each of said voids being within the range of about 0.5 mm and 10 mm, with the average depth of each of said voids being in the range of 0.2 mm to 4 mm, and with each of said voids being resistant to collapse in the presence of liquids in the wound to maintain empty space therein, said plurality of voids occupying more than about 25% of the surface area of said first surface, wherein each of said first surface, said second surface and said wound surface contact elements comprises the same fibrous material;
   b. applying said dressing on the wound so that said first surface is in engagement with the tissue of the mammal at the wound;
   c. providing a conformable cover comprising an adhesive film arranged for forming a conformable seal with the tissue of the mammal adjacent the wound without applying any adhesive to the wound;
   d. applying said cover over said second surface of said dressing to establish a confined space in which said dressing is located and to cause said first surface of said dressing to be in intimate engagement with the tissue of the mammal at the wound;
   e. providing a vacuum source;
   f. applying and maintaining suction in discrete periods of time over at least a several day period of time from said vacuum source to said confined space by coupling said vacuum source to said confined space to produce a compressive force on said dressing while maintaining empty space within said voids extending to within the range of about 0.2 mm to 5 mm above the surface of the wound, whereupon a force in a force range of 0.1 PSI to 5.0 PSI is applied on the tissue at said voids by the suction without completely collapsing said voids, which force encourages cellular activity within said voids, thereby facilitating wound healing; and g. maintaining said dressing in intimate engagement with the tissue of the mammal at the wound during the application of suction thereto.

26. The method of claim 25, wherein said permeable structure consists essentially of said fibrous material.

* * * * *